(12) United States Patent
Bitong et al.

(10) Patent No.: US 12,240,652 B2
(45) Date of Patent: Mar. 4, 2025

(54) CONTAINERS AND SYSTEMS FOR USE DURING EXTERNAL STERILIZATION OF DRUG DELIVERY DEVICES

(71) Applicant: AMGEN INC., Thousand Oaks, CA (US)

(72) Inventors: Anthony Bitong, Calabasas, CA (US); Jessica Liu, Agoura Hills, CA (US); Mads Schjoth Due, Lyngby (DK); Wael Mismar, Redondo Beach, CA (US); Greg Payne, Plymouth, IN (US)

(73) Assignee: AMGEN INC., Thousand Oaks, CA (US)

( * ) Notice: Subject to any disclaimer, the term of this patent is extended or adjusted under 35 U.S.C. 154(b) by 277 days.

(21) Appl. No.: 17/183,515

(22) Filed: Feb. 24, 2021

(65) Prior Publication Data
US 2021/0261297 A1    Aug. 26, 2021

Related U.S. Application Data

(60) Provisional application No. 62/980,898, filed on Feb. 24, 2020.

(51) Int. Cl.
*B65D 25/04* (2006.01)
*A61L 2/00* (2006.01)

(52) U.S. Cl.
CPC ............ *B65D 25/04* (2013.01); *A61L 2/0094* (2013.01); *A61L 2202/122* (2013.01); *A61L 2202/23* (2013.01); *B65D 2501/24* (2013.01)

(58) Field of Classification Search
CPC ........................ A61L 2202/23; A61L 2202/122
(Continued)

(56) References Cited

U.S. PATENT DOCUMENTS 4,523,679 A * 6/1985 Paikoff ..................... A61L 2/04
206/439
6,493,917 B1 * 12/2002 Sunka .................. A47B 88/994
312/348.3
(Continued)

FOREIGN PATENT DOCUMENTS

EP          0681963 A1     11/1995
JP        2005506110 A      3/2005

OTHER PUBLICATIONS

Hurley et al., Packaging for parcel post NBS IR 74-617, NIST, National Institute of Standards and Technology, 214 pp. (Dec. 31, 1974).
(Continued)

*Primary Examiner* — Stephen J Castellano

(57) ABSTRACT

A container and systems for use during an external sterilization process of a plurality of drug delivery devices are provided. The container may include an outer housing and at least one partition at least partially enclosed by the outer housing. The at least one partition may include a plurality of first dividers and a plurality of second dividers. The at least one partition may also be positioned an open configuration, wherein the plurality of first dividers and the plurality of second dividers cooperate with each other to define a plurality of chambers configured to receive at least one of the plurality of drug delivery devices. The at least one partition may also be positioned in a closed configuration wherein the plurality of chambers are substantially completely collapsed.

21 Claims, 7 Drawing Sheets

(58) Field of Classification Search
USPC .......................................................... 220/501
See application file for complete search history.

(56) References Cited

U.S. PATENT DOCUMENTS

| | | | | |
|---|---|---|---|---|
| 7,410,094 | B2* | 8/2008 | Bos | B65D 5/48038 |
| | | | | 229/120.36 |
| 7,832,585 | B2 | 11/2010 | Sambrailo | |
| 2003/0222129 | A1* | 12/2003 | Williams | B65D 5/48004 |
| | | | | 229/120.31 |
| 2005/0238530 | A1* | 10/2005 | Frieze | A61B 50/34 |
| | | | | 422/1 |
| 2006/0196193 | A1* | 9/2006 | Byrne | B01L 9/52 |
| | | | | 62/62 |
| 2014/0027333 | A1 | 1/2014 | Pawlowski et al. | |
| 2015/0209230 | A1* | 7/2015 | Lev | A61J 1/20 |
| | | | | 604/414 |
| 2018/0201404 | A1 | 7/2018 | Lam et al. | |
| 2020/0030470 | A1* | 1/2020 | Mauzerall | A61L 2/07 |

OTHER PUBLICATIONS

International Application No. PCT/US2021/019317, International Search Report and Written Opinion, mailed Jun. 4, 2021.

* cited by examiner

CONTAINERS AND SYSTEMS FOR USE DURING EXTERNAL STERILIZATION OF DRUG DELIVERY DEVICES

CROSS-REFERENCE TO RELATED APPLICATION

The present application claims priority to U.S. Application No. 62/980,898, filed Feb. 24, 2020. The priority application is hereby incorporated by reference in its entirety.

FIELD OF THE INVENTION

This disclosure generally relates to drug delivery devices. More particularly, the disclosure generally relates to containers and systems for use during external sterilization of drug delivery devices.

BACKGROUND

As is known in the art, syringes are medical delivery devices used to administer a medicament to a patient. Syringes are often marketed either in pre-filled form, wherein a set dosage or amount of medicament may be provided therein, or they are empty and intended to be filled from a vial or other source of medicament by an end user at the time administration of the medicament is desired. In either case, syringes often include a barrel portion adapted to retain the medicament, a conventional piercing element such as a needle, a plunger rod, an elastomeric or rubber-like stopper element fitted in a substantially fluid-tight manner within the interior of the barrel, and a flange around the open proximal end of the syringe barrel as a form of finger rest to facilitate a user's manipulation of the device.

It may be desirable, both for integrity of the medicament as well as for patient safety, to sufficiently sterilize the components of the syringe. Sterilization may occur at several stages in the assembly process, including pre-fill stages (e.g., sterilization of the empty barrel and/or plunger) and post-fill stages (e.g., external sterilization of the assembled pre-filled syringe). External sterilization typically occurs after the pre-filled syringe has been filled, fully assembled, and located in at least some portion(s) of its final packaging (e.g. a blister pack). For some indications of use, such as certain ophthalmic indications, federal regulations may require external sterilization under certain conditions, parameters, and/or results.

External sterilization may pose design challenges. For example, medicament may be sensitive to sterilization and/or conditions thereof, such as temperatures, gases, and/or radiation. As a more specific example, it may be desirable, advantageous, or necessary for external sterilization to occur under conditions that are relatively time-consuming, such as performing one or more of the sterilization steps for a longer period of time than would be possible while operating at a higher temperature and/or a higher dose that would be suitable for an un-filled container. Therefore, it may be advantageous or desirable to sterilize a plurality of devices at a time to reduce processing time and/or improve efficiency. As another example, surface interactions between the devices, between the devices and their packaging, and/or between various packages (e.g. between blister packs) may create or promote occluded spaces that may not be sterilized effectively and/or completely during external sterilization steps performed on the syringe. Therefore, it is desirable to maintain integrity of the medicament while reaching a suitable level of sterilization for all relevant devices, packaging, and respective portions thereof.

The present disclosure sets forth methods embodying advantageous alternatives to existing external sterilization methods, and that may address one or more of the challenges or needs mentioned herein, as well as provide other benefits and advantages.

SUMMARY

A container and systems for use during an external sterilization process of a plurality of drug delivery devices are provided. The container may include an outer housing and at least one partition at least partially enclosed by the outer housing. The at least one partition may include a plurality of first dividers and a plurality of second dividers. The at least one partition may be positionable in an open configuration and a closed configuration. In the open configuration, the plurality of first dividers and the plurality of second dividers cooperate to define a plurality of chambers configured to receive at least one of the plurality of drug delivery devices. In the closed configuration, the plurality of chambers are substantially completely collapsed.

In some examples, in the first configuration, the first dividers and the second dividers may be arranged generally perpendicular to each other. In some examples, while the at least one partition is positioned in the open configuration, the at least one partition has a length and a width dimension substantially equal to a length and a width dimension of the outer housing.

In some forms, when the partition is positioned in the closed configuration, the partition may have a length and/or a width dimension that is less than half of a corresponding length and/or a width dimension of the outer housing. In some examples, when the partition is positioned in the closed configuration, the partition may have a length and/or a width dimension that is less than one quarter of a corresponding length and/or a width dimension of the outer housing. In yet other examples, when the partition is positioned in the closed configuration, the partition may have a length and/or a width dimension that is less than one-eighth of a corresponding length and/or a width dimension of the outer housing.

In some examples, each of the plurality of drug delivery devices includes a pre-filled syringe within a blister pack. In some examples, each of the plurality of chambers may define a chamber volume. When the at least one partition is positioned in the open configuration, the chamber volume may be a non-zero value, and when the at least one partition is positioned in the closed configuration, the chamber volume may be zero.

In accordance with a second aspect, a container for use during an external sterilization process of a plurality of drug delivery devices is provided. The container may include an outer housing and at least one partition at least partially enclosed by the outer housing. The at least one partition may define a plurality of chambers each being configured to receive at least two of the plurality of drug delivery devices in a front to back configuration. The container may be configured to receive at least 180 drug delivery devices, at least 360 drug delivery devices, at least 540 drug delivery devices, or at least 720 drug delivery devices.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

DETAILED DESCRIPTION

The present disclosure generally relates to injection devices which can be safely and reliably utilized by a user for administering a drug, or in the case where a patient is the user, self-administering a drug. More particularly, the disclosure generally relates to a container for use during an external sterilization process of a plurality of drug delivery devices. As an example, the container may support or hold a plurality of drug delivery devices during at least some steps of the external sterilization process: (1) holding or supporting the drug delivery devices while they are being transported to a sterilization chamber, (2) holding or supporting the drug delivery devices while they are within the sterilization chamber during the sterilization step, (3) holding or supporting the drug delivery devices while they are being removed from the sterilization chamber after the sterilization step, and/or (4) any other step where the drug delivery devices are being transported or supported. The injection devices may be in the form of a syringe, such as a pre-filled syringe and/or a pre-filled syringe positioned within primary packaging, such as a blister pack. Utilizing the containers and systems set forth herein, as well as variations of the same, one may be able to utilize a desired bioburden kill level while minimizing or avoiding inefficiencies in the process and/or undesirable effects on the medicament.

The term "about" as used herein means+/−10% to the smallest significant digit.

Figure 1:
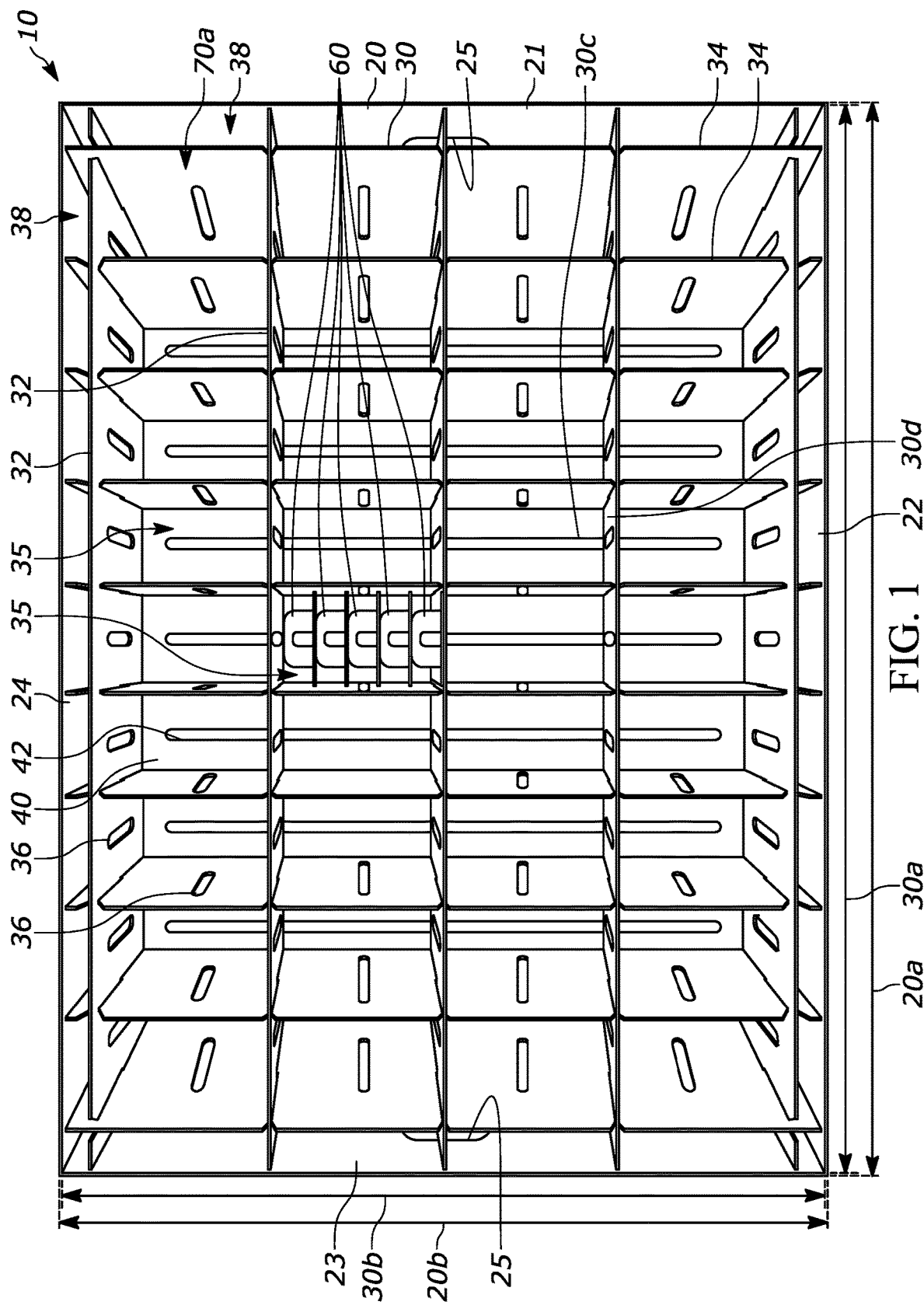
FIG. 1 is an isometric view of an example container for use during an external sterilization process of a plurality of drug delivery devices, embodying aspects of the present disclosure, where the container includes five drug delivery devices positioned within a chamber of the container.

Turning to the Figures, FIG. 1 illustrates a container 10 for use during external sterilization process of a plurality of drug delivery devices 60. The container includes an outer housing 20 and at least one partition 30 at least partially enclosed by or otherwise disposed within the outer housing 20. The outer housing 20 shown in FIG. 1 is generally rectangular parallelepiped shaped (also known as a rectangular prism or a rectangular cuboid) having four side walls 21, 22, 23, 24, a bottom wall (not labeled in FIG. 1), and a top wall (not shown in FIG. 1 for illustrative purposes) cooperating to define an inner volume. The outer housing 20 shown in FIG. 1 includes openings 25 to permit and/or facilitate entry of sterilization gas into the inner volume of the outer housing 20. The openings 25 may also be positioned and sized such as to serve as handles for the container 10. As a more specific example, the openings 25 shown in FIG. 1 are large enough to each fit a person's hand and are spaced generally across from each other (e.g., on the first and third side walls 21, 23 or on the second and fourth side walls 22, 24) to serve as balanced carrying points. The outer housing 20 may be made of any suitable material, such as polypropylene, polycarbonate, polyethylene, acrylonitrile butadiene styrene (ABS), polytetrafluoroethylene (PTFE)/Teflon, other fluoropolymers, other thermoplastic polymers, or another material or combination of materials that compatible with sterilization gas and medical products utilized while also providing sufficient structural support while being relatively lightweight. As a more specific example, the outer housing may be made of HDPE (High Density Polyethylene) and/or may include a corrugated design to increase component strength and/or durability.

Although FIG. 1 only shows two openings 25, the outer housing 20 may have more openings of similar or varying size and shape positioned along various portions of the outer housing 20, including but not limited to the side walls 21, 22, 23, 24; the bottom wall; and/or the top wall. For example, the outer housing 20 may include: between approximately 4 and 60 openings, between approximately 8 and 50 openings, between approximately 12 and 40 openings, between approximately 16 and 36 openings, between approximately 20 and 30 openings, and/or between approximately 24 and 28 openings. The openings may be generally evenly spaced apart from each other or they may be concentrated on certain portions of the outer housing 20, such as on the side portions more so than the top and bottom portions. The openings 25 may be spaced apart from each other and sized such as to facilitate distribution of sterilization gas while also providing a desired amount of structural stability for the container and/or the drug delivery devices 60 located therein. The openings 25 may have any suitable size, such as a length of approximately 2 inches and a width of approximately one-half inch. As another example, the openings 25 may be larger such as a length of approximately 2 inches and a width of approximately 2 inches and a generally rounded shape. As yet another example, the openings 25 may have a length of approximately 2.5 inches and a width of approximately 2.5 inches. As another example, the openings 25 may have a length of approximately 3 inches and a width of approximately 3 inches.

The outer housing 20 may also include features to permit nesting of additional outer housing when not in use, such as a tapered construction, a collapsible design, or other features that minimize space when not in use. The outer housing 20 may also or alternatively be chemically resistant to alkalis, oils, acids, and/or detergents.

The container 10 includes at least one partition 30 at least partially enclosed by the outer housing 20. For example, the partition 30 shown in FIG. 1 is enclosed within the inner volume defined by the outer housing 20. As a more specific example, the partition 30 shown in FIG. 1 has a length dimension and a width dimension that are slightly smaller than the corresponding length and width dimensions of the inside of the outer housing. As an even more specific example, the outer housing 20 shown in FIG. 1 has a length 20a of approximately 25.1 inches and a width 20b of approximately 19.6 inches. The partition 30 shown in FIG. 1 has a length 30a of approximately 25 inches and a width 30b of approximately 19.5 inches. The outer housing 20 and the partition 30 may have any other suitable lengths and widths, preferably as long as the partition 39 is able to fit within the outer housing 20. The outer housing 20 may have dimensions that correspond to the size of a sterilization chamber so that the container 10 is able to fit within the chamber without wasting space.

The container 10 shown in FIG. 1 includes a partition 30 with a plurality of first dividers 32 each generally extending in a first direction and a plurality of second dividers 34 each generally extending in a second direction that is substantially perpendicular to the first direction. As a more specific example, the first dividers 32 extend substantially parallel with the side walls 22, 24 and the second dividers 34 extend substantially parallel with the side walls 21, 23, but the dividers 32, 34 may extend at other suitable angles with respect to the outer housing 20. The partition 30 shown in FIG. 1 includes five of the plurality of first dividers 32 and ten of the plurality of the second dividers, but any other suitable number of dividers may be utilized. For example, the partition 30 may include: between one and 20 of the plurality of the first dividers 32 and between one and 30 of the second dividers 34, between two and 10 of the plurality of the first dividers 32 and between two and 20 of the second dividers 34, between three and eight of the plurality of the first dividers 32 and between four and 16 of the second dividers 34, between four and six of the plurality of the first dividers 32 and between six and 12 of the second dividers 34, or any other suitable number of dividers.

The first and second dividers 32, 34 cooperate with each other to define chambers 35 configured to receive drug delivery devices 60. For example, the first and second dividers 32, 34 of the partition 30 define thirty-six (36) chambers, but any other suitable number of chambers 35 may be utilized. For example, the partition 30 may define between about 10 and 60 chambers 35, between about 24 and 48 chambers 35, between about 30 and 42 chambers 35, or any other suitable number of chambers 35.

Figure 6:
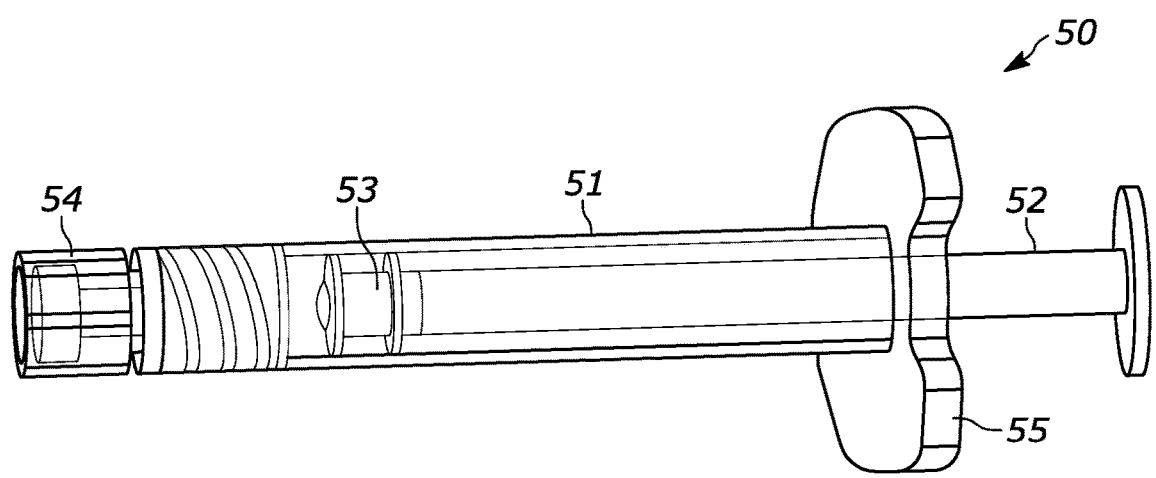
FIG. 6 is a top view of an example drug delivery device, more specifically a pre-filled syringe, suitable for use with the example container embodying aspects of the present disclosure.
Figure 7:
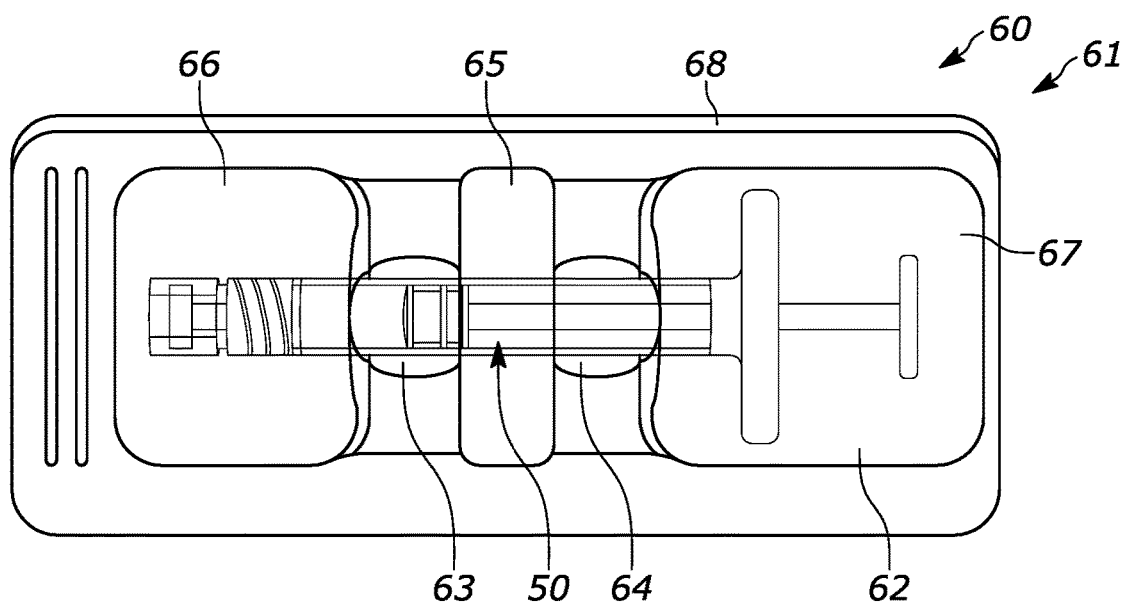
FIG. 7 is a top view of an example drug delivery device, more specifically a pre-filled syringe disposed within a blister pack, located within packaging suitable for use with the example container embodying aspects of the present disclosure.

In the container 10 shown in FIG. 1, each chamber 35 is configured to receive approximately five drug delivery devices 60. As a more specific example, each of the drug delivery devices 60 shown in FIG. 1 includes a pre-filled syringe 50 within a blister pack 61 (FIGS. 6-7). As an example, the pre-filled syringe 50 includes a barrel 51, a plunger rod 52, a stopper 53, a luer lock cap 54, and a backstop 55. As an example, the blister pack 61 generally includes a tray 62 and a cover 68. As a more specific example, the blister pack 61 may include two pairs of flanges 63, 64, such as snap-fit flanges, to support and/or hold the pre-filled syringe barrel 51 as well as chambers 65, 66, 67 for permitting a user to grip the pre-filled syringe 50 and/or to permit room for components such as the backstop 55. Alternatively or additionally, the pre-filled syringe 50 may be squeezed or pressed out of the tray via the backside of the tray.

The blister pack tray 62 may be coupled with the cover 68. As a more specific example, the blister pack tray 62 may be sealed with the cover 68 after the pre-filled syringe 50 is filled and assembled. The blister pack tray 62 may be made of any suitable material, such as Polyethylene Terephthalate Glycol Copolymer (PETG) and the cover 68 may be made of any suitable material, such as Tyvek or any suitable medical paper. The cover 68 shown in FIG. 1 is gas porous to permit, during the external sterilization step, entry (and exit) of the sterilization gas into and out of the internal chamber defined by the blister pack tray 62 and the cover 68. As a more specific example, the cover 68 includes micropores such that the cover 68 may be gas permeable to facilitate external sterilization of the pre-filled syringe 50 while it is in the blister pack 60. As an even more specific example, the blister pack tray 62 may not be gas permeable, such that the sterilization gas may travel through the cover 68 but not through the blister pack tray 62.

As mentioned above, the drug delivery devices 60 shown in FIG. 1 include a pre-filled syringe 50 positioned within a blister pack 61 (e.g. the tray 62 which has been sealed with the cover 68) so that the drug delivery devices 60 are ready for the step of external sterilization. The drug delivery devices 60 are positioned with respect to each other such that the cover 68 of one device 60 abuts and/or is adjacent to the blister pack tray 62 of an adjacent device (e.g. front to back configuration). This configuration helps facilitate entry and exit of the sterilization gas into the internal chamber defined by the blister pack tray 62 and the cover 68. As a more specific example, if adjacent devices were arranged such that the respective covers 68 would abut each other, the respective covers could potentially block or prevent entry of sterilization gas into the internal chamber defined by the blister pack tray 62 and the cover 68.

Each of the dividers 32, 34 shown in FIG. 1 includes a plurality of openings 36 to help facilitate distribution of sterilization gas within the container 10. For example, each of the plurality of first dividers 32 shown in FIG. 1 includes nine openings 36 and each of the plurality of second dividers 34 shown in FIG. 1 includes four openings 36. However, the dividers 32, 34 may include any other suitable number of openings 36. For example, each of the plurality of first dividers 32 may include between about one and 20 openings 36 and each of the plurality of second dividers 34 may include between about one and 10 openings 36; each of the plurality of first dividers 32 may include between about two and 16 openings 36 and each of the plurality of second dividers 34 may include between about one and eight openings 36; each of the plurality of first dividers 32 may include between about four and 12 openings 36 and each of the plurality of second dividers 34 may include between about two and six openings 36; each of the plurality of first dividers 32 may include between about six and 10 openings 36 and each of the plurality of second dividers 34 may include between about three and five openings 36. The openings 36 may be spaced apart from each other and sized such as to facilitate distribution of sterilization gas while also providing a desired amount of structural stability for the container and/or the drug delivery devices 60 located therein. For example, the openings 36 may have a length of approximately 2 inches and a width of approximately one-half inch. As another example, the openings 36 may be larger such as a length of approximately 2 inches and a width of approximately 2 inches and a generally rounded shape. As yet another example, the openings 36 may have a length of approximately 2.5 inches and a width of approximately 2.5 inches. As another example, the openings 36 may have a length of approximately 3 inches and a width of approximately 3 inches.

As shown in FIG. 1, the partition 30 and the outer housing 20 cooperate to define a series of peripheral chambers 38 near the inner wall periphery of the outer housing 20. As a more specific example, the peripheral chambers 38 are each smaller than the chambers 35 for holding the drug delivery devices 60 and the peripheral chambers 38 do not house or hold the drug delivery devices 60 but rather act as spacers between the outer housing 20 and the chambers 38 to prevent occlusion of gas and to serve as a protective barrier to prevent loading on and to protect the blister packs 61. As a more specific example, the peripheral chambers 38 create a buffer space between the inner wall of the outer housing 20 and the outermost dividers 32, 34 which are parallel to the inner wall of the outer housing 20 to prevent or minimize the amount of gas that is trapped therebetween.

Figure 5:
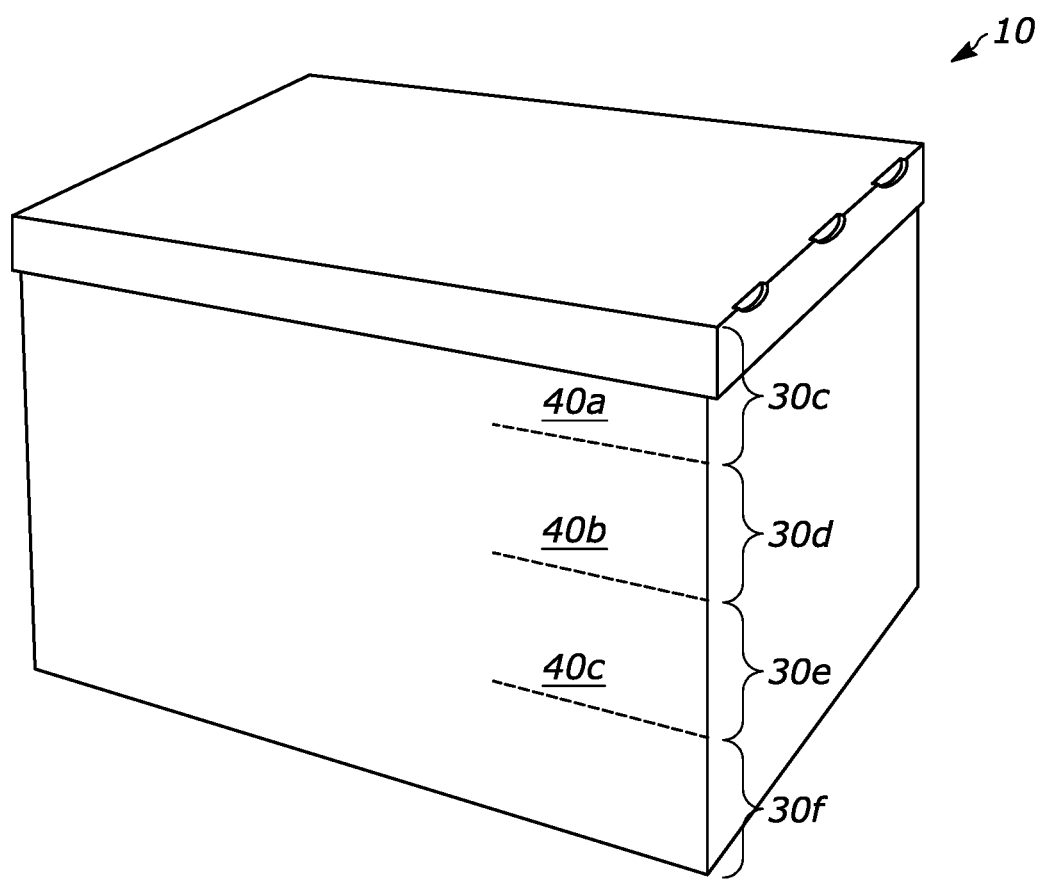
FIG. 5 is an isometric view of an example container for use during an external sterilization process of a plurality of drug delivery devices, embodying aspects of the present disclosure, where the container includes a top cover.

The container 10 may include more than one partition 30. For example, the container 10 shown in FIG. 1 includes four (4) partitions, stacked vertically on each other and separated by level dividers 40. As a more specific example, the topmost partition 30c and the second topmost partition 30d are visible in FIG. 1 and are separated by the level divider 40. The partitions 30c, 30d, 30e, 30f (FIG. 5) are each similar or identical to each other and the different dividers 40a, 40b, 40c (FIG. 5) are each similar or identical to each other such that each partition 30c-30f is able to support and hold the same number of drug delivery devices 60. As a more specific example, the partition 30c shown in FIG. 1 includes 36 chambers 35 and each chamber 35 is able to support and hold five drug delivery devices 60, so that partition 30c is able to support and hold up to 180 drug delivery devices 60. Therefore, each of the subsequent partitions 30d-30f each is also able to support and hold up to 180 drug delivery devices 60, for a total of 720 drug delivery devices 60 (e.g., 180*4=720).

The level dividers 40 each include a plurality of openings 42 that permit and facilitate distribution of sterilization gas between the various partitions 30c-30f. As a more specific example, the openings 42 shown in FIG. 1 each extend substantially (but not completely) along a width of the level dividers 40 such that each chamber 35 includes a corresponding portion of the opening 42 to permit and facilitate communication with the chambers above and/or below. As an alternative or additional example, the openings may extend along the length (e.g., along line 30a and 20a) instead of along the width (e.g., along line 30b and 20b). As yet alternative or additional example, the openings may each be discrete openings rather than extending along the length or width of multiple chambers 35.

The level dividers 40 may be each be sized and shaped similar to the partitions 30, or slightly smaller than the same to permit or facilitate gas distribution among the different peripheral chambers 38. The level dividers 40 may be made of the same or similar materials as the plurality of first dividers 32 and/or the plurality of second dividers 34 and/or the outer housing 20.

Figure 2:
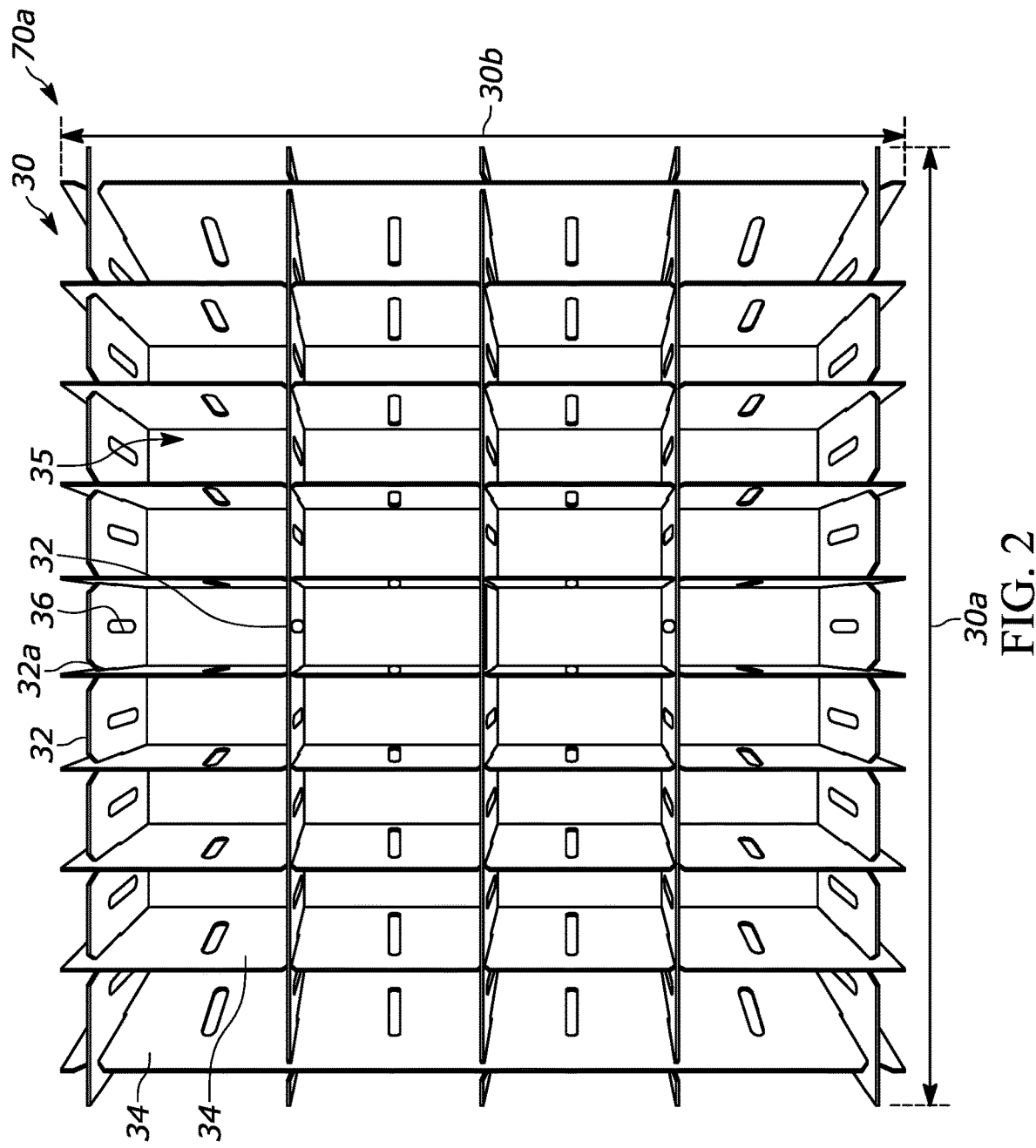
FIG. 2 is an isometric view of an example partition suitable for use with a container such as the example container shown in FIG. 1, embodying aspects of the present disclosure, where the partition is positioned in an open configuration.
Figure 3:
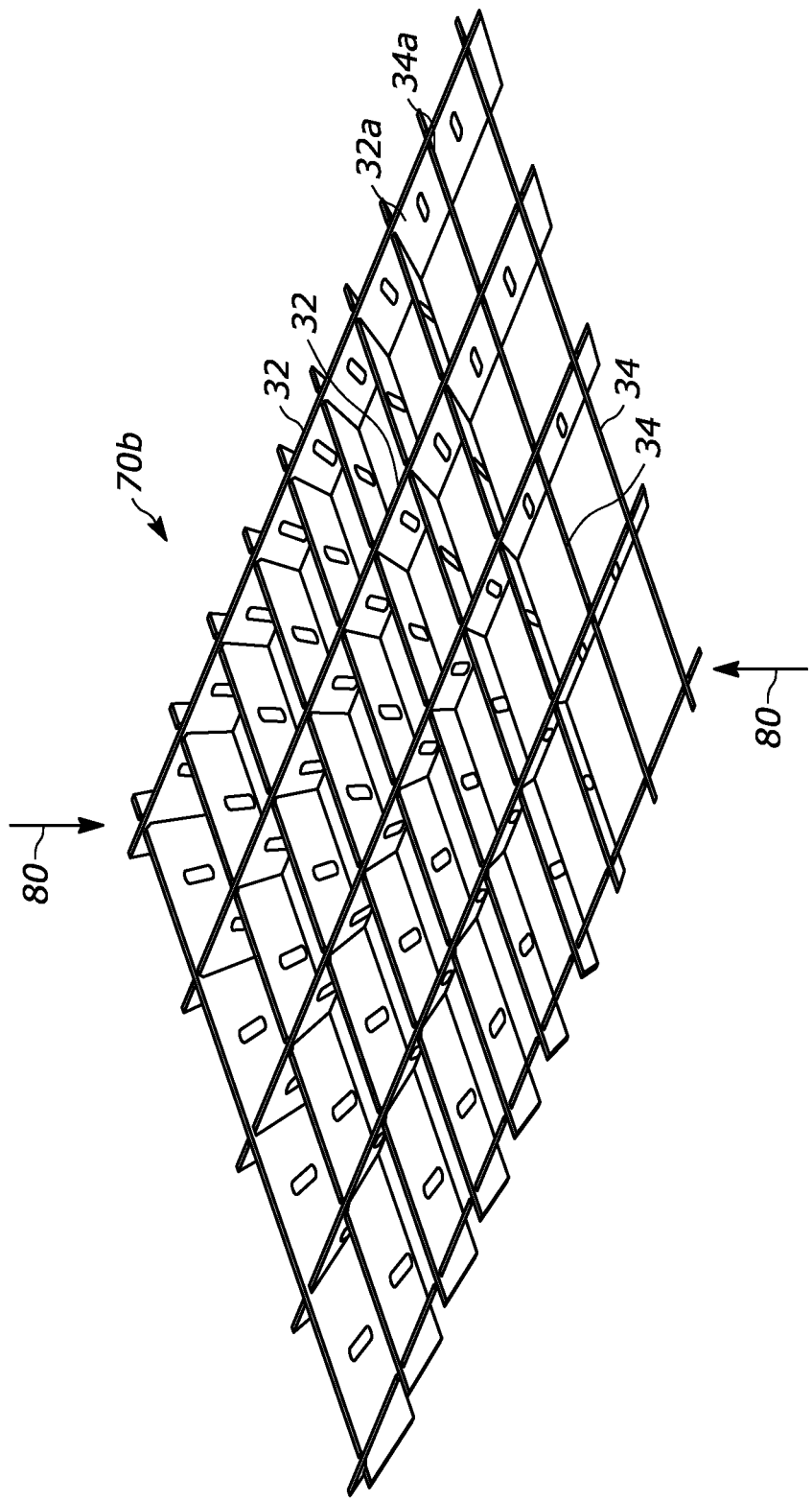
FIG. 3 is an isometric view of the example partition shown in FIG. 2, where the partition is positioned in a partially-closed configuration.

The partitions 30 each may be positionable between an open configuration 70a (FIGS. 1-2) and a closed configuration 70c (FIGS. 4A and 4B), as well as potentially an intermediate configuration 70b (FIG. 3). For example, the partitions 30 may be positioned in the open configuration 70a when the partitions 30 are positioned within the container 10 or about to be loaded in the container 10. As another example, the partitions 30 may be positioned in the closed configuration 70c when the partitions 30 are not being used or are in a storage/non-use state.

When the partitions 30 are positioned in the open configuration 70a, the chambers 35 are configured to be able to receive the intended number drug delivery devices 60, such as five units shown in FIG. 1. As another example, when the partitions 30 are positioned in the open configuration 70a, the chambers 35 may have their maximum volume or another volume that is substantially equal to their maximum volume. In other words, when the partitions 30 are positioned in the open configuration 70a, the chambers 35 may be fully open or fully expanded.

Figure 4A:
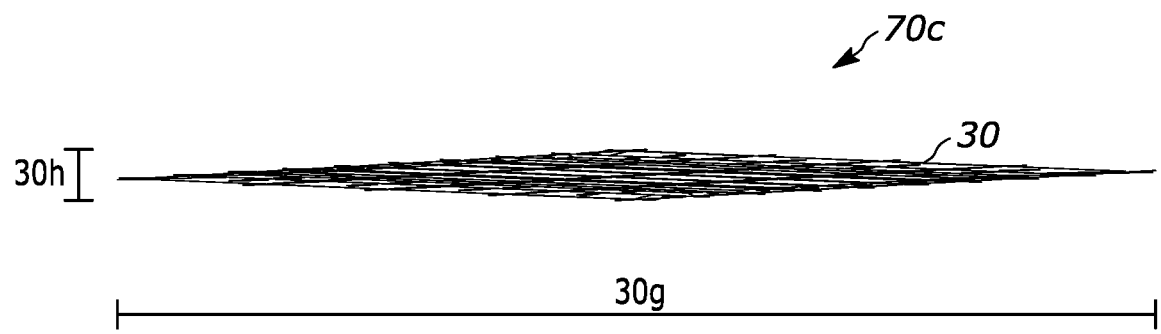
FIG. 4A is a top view of the example partition shown in FIGS. 2 & 3, where the partition is positioned in a closed configuration.

When the partitions 30 are positioned in the closed configuration 70c, the chambers 35 are configured to not be able to receive the drug delivery devices 60. Also, the chambers 35 may be at or near their minimum volume, meaning they may have no volume. In other words, when the partitions 30 are positioned in the closed configuration 70c, the chambers 35 may be fully closed or minimized. When the partitions 30 are positioned in the closed configuration 70c, as shown in FIG. 4A, the closed length 30g and/or the closed width 30h of the partitions 30 may be much different than those dimensions for the partition 30 in the open configuration 70a. For example, the closed length 30g of the partition 30 when positioned in the closed configuration 70c is longer than the length 30a of the partition 30 when positioned in the open configuration due to the fact that the various dividers 32 are off-set from each other in a stair-step fashion. As another example, the closed width 30h of the partition 30 when positioned in the closed configuration 70c is shorter than the width 30b of the partition 30 when positioned in the open configuration 70a because the dividers 34 are compressed against each other.

The dividers 32, 34 may include mating notches 32a, 34a (FIG. 3) that facilitate movement between the respective dividers 32, 34. As a more specific example, the top portions of the dividers 34 may include notches that extend from the top to a middle portion along the height of the divider 34 and the bottom portions of the dividers 32 may include notches that extend from the bottom to a middle portion along the height of the divider 32, or vice versa. Alternative designs for interfaces between the dividers 32, 34 may be utilized. The notches 32a, 34a may have a thickness that promotes easy, quick movement between the various configurations 70a, 70b, 70c, such that the partition 30 has a "quick collapse" design. For example, the partition 30 may be collapsed by applying a force on one or more corners of the partition 30, such as indicated by arrows 80 in FIG. 3.

The closed configuration 70c for the partition 30 may be suitable for reducing shipping or storage footprints/space requirements while also facilitating quick assembly of the container 10.

Figure 8:
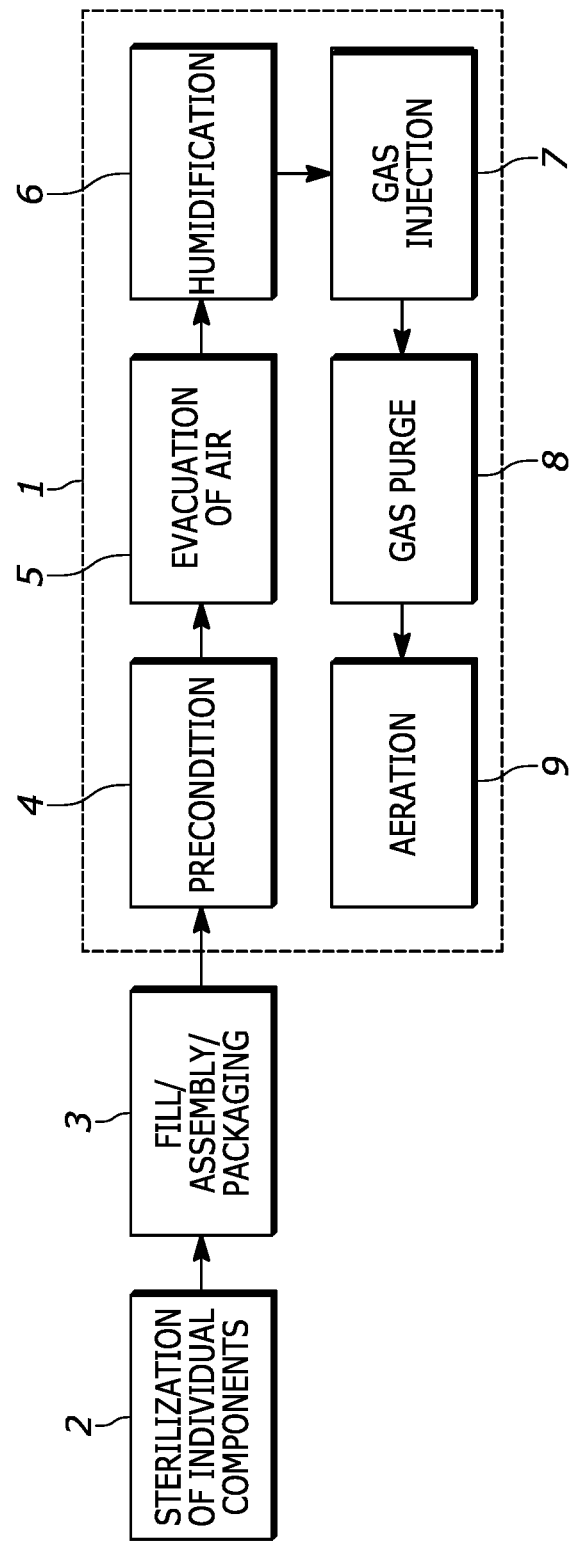
FIG. 8 is an exemplary method or series of steps for assembling and externally sterilizing a drug delivery device embodying aspects of the present disclosure.

With reference to FIG. 8, an exemplary method of assembling and externally sterilizing a drug delivery device according to an embodiment of the present disclosure is provided. During a first step, in box 2, at least some individual components of a drug delivery device are sterilized, often prior to receipt by the manufacturing facility. For example, the syringe barrel and plunger stopper, and any other components that may have direct contact with the drug product, may be sterilized during this step. This step may utilize a variety of known techniques for sterilizing various unassembled components of the drug delivery device, including but not limited to components shown in FIGS. 6-7. During a second step, in box 3, the barrel is filled and the stopper (a.k.a. the "plunger stopper") is assembled with the barrel. The assembly step may also include adding at least some of the following: a plunger rod, a flange extender, a tip cap with a Luer Lock, a needle, a rigid needle shield, and/or a backstop such as those shown in FIGS. 2-6. At least some of these components may be pre-assembled with each other, but they may also be assembled at the filling line, such as if the filling process is performed aseptically. Also, the syringe typically will either have a tip cap Luer Lock tip or a mounted (e.g., staked) needle rather than having both components. The syringe may also receive any necessary or labeling during this step. Next, the external sterilization steps, designated by dotted line box 1, proceed. It may be appropriate and/or desirable to utilize the container 10 during some or all of the steps designated by dotted line box 1, or during additional steps described herein.

In box 4, the syringes are preconditioned. For a process utilizing Nitrogen Dioxide (NO2), preconditioning may include at least some or all of the following steps: removing the samples from storage, allowing the syringes to adjust to room condition equilibration for a desired amount of time (such as 30 minutes, 90 minutes, 2 hours, or any desirable amount of time), and placing the syringes into a sterilization chamber. Preconditioning may occur inside or outside of the chamber.

When utilizing Ethylene Oxide (EtO), the precondition step (box 4) may vary slightly than the step described for NO2. For example, the syringes may be preconditioned inside of the sterilization chamber (without gas injection) for 360 minutes (or another desirable length of time). However, as with the process utilizing NO2, the preconditioning step utilizing EtO may occur inside or outside of the chamber.

Next, for box 5, the sterilization chamber either remains closed (if preconditioning occurred inside the chamber) or the container 10 is placed inside the chamber and the chamber is closed. Then, all or substantially all of the air is evacuated from the chamber. The air evacuation step may be performed in multiple pulses/steps, as this may assist with controlling the initial humidity within the chamber. Next, in box 6, the sterilization chamber is humidified to a desired setting, such as 75 or 80 (or any desired amount of percentage of relative humidity). In some processes, boxes 6 and 7 may be swapped, so that the sterilization gas is injected before humidity is increased.

Next, in box 7, the desired sterilization gas is injected and held in the chamber for a desired dwell time. For recipes utilizing NO2, the gas injection step 7 may include some or all of the following steps: delivering a dose of NO2 by pulling a vacuum in the chamber for a desired amount of times followed by injecting a desired amount of gas (dose concentration) and adjusting the humidity increasing the pressure in the chamber, keeping this condition for a desired amount of time (i.e. dwell time) allowing the sterilant to get in contact with the surfaces, and then repeating these steps for a desired number of pulses. Once the number of desired pulses are complete, the gas is then finally purged (box 8) so that the gas is removed from the sterilization chamber. Finally, in box 9, the chamber is aerated for a desired number of cycles (a.k.a. "Aeration Exchanges") to ensure that all or substantially of the sterilization gas has been flushed from the syringe and packaging. The steps in boxes 8 and 9 may be combined into a single step, such that the sterilization gas is purged via aeration exchanges. In some examples, the vacuum level may vary during these steps. For example, the vacuum during dwell time may be minimal, such as approximately 590 Torr.

The method may include any suitable parameters for steps 7 thru 9, such as:

The vacuum level may be between about 20 and 500 Torr, between about 150 and 400 Torr, between about 150 and 300 Torr, or another suitable vacuum level.

The concentration of the dose of the NO2 may be between about 2 and 20 milligrams per Liter, between about 2 and 10 milligrams per Liter, between about 2 and 7 milligrams per Liter, or another suitable concentration of the dose.

The chamber may have a relative humidity of between about 70 and 90 percent or another suitable humidity.

The dwell time may be between about 2 and 20 minutes, between about 2 and 12 minutes, between about 2 and 7 minutes, or another suitable dwell time.

The number of pulses may be between about 1 and 24, between about 1 and 12, between about 1 and 8, between about 1 and 4, between about 1 and 2, or another suitable number of pulses.

The step of aerating the sterilization chamber may include aerating the sterilization chamber a number of cycles between about 12 and 70 or another suitable number of cycles.

As a more specific example, Table 1 shows different variables for ten different exemplary recipes for sterilizing a drug delivery device utilizing Nitrogen Dioxide (NO2):

TABLE 2

| Vacuum (Torr) | NO2 Dose (mg/L) | Relative Humidity (%) | Dwell Time (mins.) | Number of Pulses | Number of Aerations |
| --- | --- | --- | --- | --- | --- |
| 20 | 10 | 75 | 10 | 8 | 12 |
| 20 | 10 | 75 | 10 | 12 | 12 |
| 20 | 10 | 75 | 10 | 24 | 12 |
| 100 | 10 | 75 | 10 | 8 | 12 |
| 100 | 10 | 75 | 10 | 12 | 12 |
| 100 | 10 | 75 | 10 | 24 | 12 |

As another example, Table 2 shows different variables for six different exemplary recipes for sterilizing a drug delivery device utilizing NO2:

TABLE 3

| Vacuum (Torr) | NO2 Dose (mg/L) | Relative Humidity (%) | Dwell Time (mins.) | Number of Pulses | Number of Aerations |
| --- | --- | --- | --- | --- | --- |
| 100 | 10 | 75 | 10 | 2 | 24 |
| 300 | 10 | 75 | 10 | 2 | 35 |
| 100 | 20 | 80 | 20 | 4 | 24 |
| 20 | 10 | 80 | 10 | 4 | 24 |
| 100 | 10 | 75 | 10 | 2 | 24 |
| 100 | 20 | 80 | 20 | 4 | 24 |
| 20 | 10 | 80 | 10 | 4 | 24 |
| 300 | 10 | 75 | 10 | 2 | 35 |
| 20 | 10 | 80 | 10 | 4 | 24 |
| 20 | 20 | 80 | 20 | 4 | 24 |

In Tables 1 and 2, the "Vacuum Level (Torr)" column label refers to the vacuum force applied on the external sterilization chamber during step 4 in FIG. 1. As shown, the vacuum force varies from 20 Torr to 500 Torr, although different vacuum forces may be appropriate. The vacuum force numbers listed are inverse to their strength, such that a 20 Torr force is stronger than a 100 Torr force, which is stronger than a 500 Torr force (ambient pressure is typically about 760 Torr). The stronger the vacuum force, the greater the chance of demonstrating kill of the target bioburden.

However, if the vacuum force becomes too high, then the process may result in undesirable effects on the medicament, such as causing the plunger to move undesirably (i.e. to move past the sterility barrier and cause a sterility breach). The "NO2 Dose (mg/L)" column refers to the concentration (in mg) of NO2 per liter of air introduced to the external sterilization chamber during step 7 in FIG. 1. As shown, the dose in Tables 1 and 2 varies between 5 and 20 mg/L, although different doses may be appropriate. The higher the dose of NO2 during this step, the faster and more completely the drug delivery device will be sterilized. However, if the dose of sterilization gas becomes too high, then the process may result in undesirable effects on the medicament, such as contaminating the inside of the drug barrel with sterilization gas (i.e., ingress of sterilization gas and/or discoloration of the syringe components). The "Relative Humidity (% RH)" column refers to the relative humidity in the external sterilization chamber during step 7 in FIG. 1. As shown, the relative humidity for each row in Tables 1 and 2 varies between 75% and 80%, although different relative humidity values may be appropriate. Increasing the relative humidity also increases the likelihood of demonstrating kill of the target bioburden. The "Dwell Time (mm:ss)" column refers to the amount of time that the drug delivery device sits in the sterilization chamber while sterilization gas is present. For Tables 1 and 2, the "Total Dwell Time" is equal to the "Dwell Time" column times the "Number of Pulses" column. For example, for the first row of Table 1, the samples would experience a Total Dwell Time of 80 minutes. As shown, the dwell times listed in Tables 1 and 2 vary between 5 and 20 minutes, although different dwell times may be appropriate. The dwell time also increases the likelihood of demonstrating kill of the target bioburden. However, if the dwell time becomes too high, then the process may result in undesirable effects on the medicament, such as contaminating the inside of the drug barrel with sterilization gas and/or undesirably affecting functionality or appearance of device components. As an example, the components may experience an undesirable level of discoloration if the dwell time becomes too high. The "Number of Pulses" column refers to the number of times during the NO2 process that the gas is injected by pulling a vacuum. As shown, the pulses for each row in Tables 1 and 2 varies from 1 to 24, although different values may be appropriate. The higher the number of pulses, the greater the chance of demonstrating kill of the target bioburden. However, if the number of pulses becomes too high, then the process may result in undesirable effects on the medicament, such as contaminating the inside of the drug barrel with sterilization gas and/or undesirably affecting functionality or appearance of device components. The column referring to "Number of Aerations" refers to the number of times that the chamber is aerated (box 9 in FIG. 1) after the gas is purged from the chamber (box 8 in FIG. 1). The exemplary process may utilize aeration exchanges of 12, 24, 28, 70, or any desirable number. Up to a certain point, by increasing the number of aerations, the manufacturer may increase the likelihood that all or substantially all of the sterilization gas is removed from the syringe and packaging (post-purge).

For each of the recipes in Tables 1 and 2 (NO2), each of the steps contained within box 1 in FIG. 1 may be performed at room temperature (25 degrees Celsius), but other appropriate temperatures may be used. However, other temperatures may be used, such as between about 2 degrees Celsius to about 8 degrees Celsius, or any other desirable temperature that does not undesirably affect the medicament.

Table 3 shows different variables for 10 different exemplary recipes for sterilizing a drug delivery device utilizing NO2:

TABLE 1

| Vacuum (Torr) | NO2 Dose (mg/L) | Relative Humidity (%) | Dwell Time (mins.) | Number of Pulses | Number of Aerations |
|---|---|---|---|---|---|
| 20 | 10 | 75 | 10 | 8 | 28 |
| 20 | 20 | 80 | 20 | 4 | 24 |
| 20 | 10 | 80 | 20 | 4 | 24 |
| 20 | 10 | 80 | 10 | 4 | 24 |
| 20 | 10 | 80 | 10 | 2 | 24 |
| 20 | 10 | 80 | 10 | 1 | 24 |
| 20 | 5 | 80 | 10 | 1 | 24 |
| 20 | 5 | 80 | 10 | 2 | 24 |
| 20 | 5 | 80 | 5 | 2 | 24 |
| 500 | 5 | 80 | 5 | 2 | 70 |

When utilizing Ethylene Oxide (EtO), the gas injection step (box 7) may vary slightly. For example, the gas injection step 7 may include some or all of the following steps: delivering a dose of EtO by pulling a vacuum in the chamber for a desired amount of time (i.e., dwell time) either before or while injecting a desired amount of gas (dose concentration), and then purging the gas. In other words, when utilizing EtO, it may be desirable to run only one pulse rather than the preferred multiple pulses discussed above for NO2. For steps 8 (gas purge) and 9 (aeration), the exemplary process utilizing EtO proceeds as described above with respect to NO2.

It may be desirable and/or required by regulations to externally sterilize an injection device during the manufacturing and/or assembly process. Additionally, some applications for pre-filled syringes (such as certain ophthalmic applications) require external sterilization. For example, 21 CFR 200.50 indicates, "Ophthalmic preparations and dispensers should be sterile." Furthermore, ANSI/AAMI ST67: 2011/(R)2017 states, "Sterilization of health care products—Requirements and guidance for selecting a sterility assurance level (SAL) for products labeled 'sterile'" and Section 4.1.1—states: "Generally an SAL value of 10-6 has been used for terminal sterilization of health care products." Furthermore, Annex A to the ST67 and EN556-1:2006 provide: "Sterilization of medical devices—Requirements for medical devices to be designated "STERILE"—Part 1: Requirements for terminally sterilized medical devices" . . . Section 4.1: "For a terminally-sterilized medical device to be designated "STERILE", the theoretical probability of there being a viable micro-organism present on/in the device shall be equal to or less than $1\times10^{-6}$." Therefore, it may be desirable and/or required for a bioburden to be less than $1\times10^{-6}$ (i.e., $1\times10\hat{1}-6$). It may also or alternatively be desirable for a bioburden to be less than another level, such as $1\times10^{-4}$ (i.e., $1\times10\hat{1}-4$).

Therefore, the disclosed embodiments herein are particularly advantageous for these types of applications. The terms "external sterilization" and/or "externally sterilize" as used herein refer to the process of sterilizing an injection device after it has been assembled. For example, the injection device shown in FIGS. 2a-2c may be externally sterilized after the syringe 10 (with a drug in the cavity 13), plunger rod 16, backstop device 20, and protective cap (not shown) have all been assembled, labeled, and blistered. During the external sterilization process, the injection device is typically placed in a sterilization chamber and exposed to a sterilization gas, such as Ethylene Oxide (EtO) or Nitrogen Dioxide (NO2) or any other suitable gas, for a predetermined length of time and other specified conditions (such as temperature, humidity, and pressure). Then, after the sterilization cycle, the sterilization gas is purged from the chamber and the injection device remains in the chamber (which is substantially or completely free of sterilization gas) for another predetermined length of time and other specified conditions (such as temperature and pressure).

Due to the engagement between the backstop portion 20 and the syringe 10 shown in FIGS. 2a-2c, sterilization gas may fail to reach occluded or partially occluded spaces between the backstop device 20 and the syringe 10 and thereby fail to fully or suitably sterilize those surfaces. Additionally, or alternatively, the sterilization gas may not be effectively purged from these occluded or partially occluded spaces, thereby exposing the drug to the sterilization gas beyond the specified sterilization step in the chamber. Either and/or both of these situations may be undesirable. As a more specific example, FIG. 2d includes various views of a syringe barrel and flange, with surfaces of the same that may be particularly susceptible to occlusion shown with dark shading. For example, a flange upper surface 12b and a barrel outer surface 11b may be particularly susceptible to occlusion due to their respective engagements with the backstop device 20.

FIGS. 3a and 3b show a backstop portion 120 according to an embodiment of the present disclosure. The backstop portion 120 includes a collar portion 130 that extends distally and annularly to a syringe flange 12. The backstop device 120 also includes a body portion 132 that defines the opening 134 and engages a top surface of the flange 12. The backstop portion 120 also includes a plurality of ridges 150 that engage the syringe 10 such that the collar inner surface 130a is spaced apart from the outer surface 12a of the flange 12 and/or the outer surface of the barrel 11. In FIGS. 3a and 3b, three ridges 150 are spaced apart from each other around the collar inner surface 130a and are more preferably generally equally spaced from each other so as to form a three-point engagement between the backstop device 120 and the syringe 10. The ridges 150 may be integrally formed in the backstop device 120 collar inner surface 130a or they may be separate components attached to the collar inner surface 130a. In either case, the ridges 150 cooperate to permit a relatively secure fit between the backstop device 120 and the syringe 10 while minimizing the occluded space between the collar inner surface 130a and the outer surface 12a of the flange 12 and/or the outer surface of the barrel 11. For example, in one embodiment the ridges 150 are the only portions of the collar inner surface 130a that engage the outer surface 12a of the flange 12. For example, in another embodiment the ridges 150 are the only portions of the collar inner surface 130a that engage the outer surface of the syringe barrel 11.

The ridges 150 shown in FIGS. 3a-3b may instead have any suitable configuration that spaces apart the collar inner surface 130a from the syringe 10. For example, in one embodiment the ridges 150 may be replaced with generally circular protrusions or lines of protrusions.

Figure 4B:
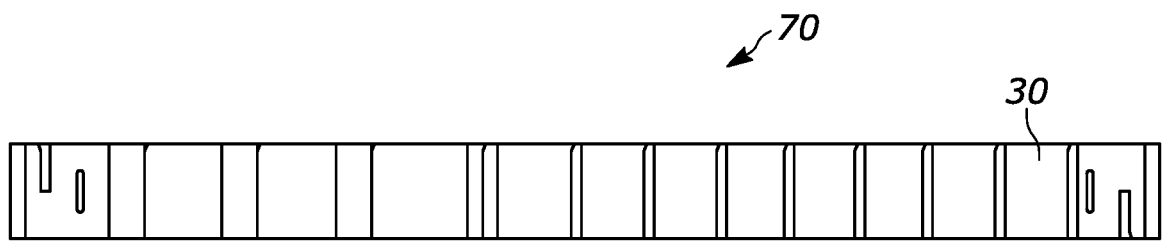
FIG. 4B is a side view of the example partition shown in FIG. 4A.

FIGS. 4a and 4b show a backstop portion 220 according to another embodiment of the present disclosure. The backstop portion 220 includes a collar portion 230 that extends distally and annularly to a syringe flange 12. The backstop device 220 also includes a body portion 232 that defines the opening 234 and engages a top surface of the flange 12. The backstop portion 220 also includes a plurality of ridges 250 that engage the syringe such that the collar inner surface 230a is spaced apart from the outer surface 12a of the flange 12 and/or the outer surface of the barrel 11. In FIGS. 4a and 4b, five ridges 250 are spaced apart from each other around the collar inner surface 230a and are more preferably generally equally spaced from each other so as to form a five-point engagement between the backstop device 220 and the syringe 10. The ridges 250 may be integrally formed in the backstop device 220 collar inner surface 230a or they may be separate components attached to the collar inner surface 230a. In either case, the ridges 250 cooperate to permit a relatively secure fit between the backstop device 220 and the syringe 10 while minimizing the occluded space between the collar inner surface 230a and the outer surface 12a of the flange 12 and/or the outer surface of the barrel 11. For example, in one embodiment the ridges 250 are the only portions of the collar inner surface 230a that engage the outer surface 12a of the flange 12. For example, in another embodiment the ridges 250 are the only portions of the collar inner surface 230a that engage the outer surface of the syringe barrel 11.

The ridges 250 shown in FIGS. 4a-4b may instead have any suitable configuration that spaces apart the collar inner surface 230a from the syringe 10. For example, in one embodiment the ridges 250 may be replaced with generally circular protrusions or lines of protrusions.

The different backstop portions 20, 120, 220 shown in FIGS. 2-4 were tested in a lethality study. For example, pre-filled syringes were "spiked" with between $1 \times 10^{\wedge}6$ and $6 \times 10^{\wedge}6$ CFU (e.g., between 1,000,000 and 6,000,000 CFU) of *Geobacillus stearothermophilus* before sterilization cycles. As a more specific example, the backstop and barrel portions of the pre-filled syringes were spiked with the $1$-$6 \times 10^{\wedge}6$ CFU of *Geobacillus stearothermophilus*. As used herein, the term "CFU" refers to "Colony-Forming Unit", which is a unit used to estimate the number of viable bacteria or fungal cells in a sample (where "viable" is the ability to multiply via binary fission under controlled conditions). *Geobacillus stearothermophilus* (previously *Bacillus stearothermophilus*) is a rod-shaped, gram-positive bacterium and a member of the division Firmicutes. The bacterium is a thermophile and is widely distributed in soil, hot springs, ocean sediment, and is a potential cause of spoilage in food products. The spiked pre-filled syringes were then sterilized using various sterilization parameters to measure the lethality of the sterilization process to evaluate the Sterility Assurance Level (SAL). The pre-filled syringes were spiked with biological indicators or direct inoculation, as is discussed in more detail below.

Notably, different backstop portions such as the backstop portions 20, 120, 220 disclosed herein were tested in the lethality study. Table 4 shows results of the lethality study evaluating the effects of NO2 based sterilization on various pre-filled syringes with the different backstop portions 20, 120, 220:

TABLE 4

| Recipe Number | Vacuum (Torr) | NO2 Dose (mg/L) | Relative Humidity (%) | Dwell Time (mins.) | Number of Pulses | Number of Aerations | Spiked Backstop | Spiked Barrel |
|---|---|---|---|---|---|---|---|---|
| PFS Samples Utilizing Backstop 20 | | | | | | | | |
| 1 | 100 | 10 | 75 | 10 | 2 | 24 | 1/5 | 5/5 |
| 2 | 300 | 10 | 75 | 10 | 2 | 35 | 0/5 | 5/5 |
| 3 | 100 | 20 | 80 | 20 | 4 | 24 | 0/5 | 5/5 |
| 4 | 20 | 10 | 80 | 10 | 4 | 35 | 2/5 | 5/5 |
| PFS Samples Utilizing Backstop 120 or 220 | | | | | | | | |
| 5 | 20 | 10 | 75 | 10 | 8 | 28 | 5/5 | 5/5 |
| 6 | 20 | 20 | 80 | 20 | 4 | 24 | 5/5 | — |
| 7 | 20 | 10 | 80 | 20 | 4 | 24 | 5/5 | — |
| 8 | 20 | 10 | 80 | 10 | 4 | 24 | 5/5 | — |
| 9 | 20 | 10 | 80 | 10 | 2 | 24 | 5/5 | — |
| 10 | 20 | 10 | 80 | 10 | 1 | 24 | 5/5 | 5/5 |
| 11 | 20 | 5 | 80 | 10 | 1 | 24 | 5/5 | 4/5 |
| 12 | 20 | 5 | 80 | 10 | 2 | 24 | 5/5 | 5/5 |
| 13 | 20 | 5 | 80 | 5 | 2 | 24 | 5/5 | 5/5 |
| 15 | 500 | 5 | 80 | 5 | 2 | 70 | 5/5 | 5/5 |

For each recipe number, five samples (or at least 5 test locations on one or more samples) were tested. Table 4 shows, in the "Spiked Backstop" and "Spiked" Barrel" columns, how many out of the 5 samples reached the target lethality for each recipe. For example, the target lethality for this test was a Sterility Assurance Level (SAL) of $1\times10^{-6}$. In other words, the target lethality for this test was 6 logs reduction in the number of bacteria present (before sterilization vs. after sterilization). As a more specific example, for Recipe Number 1, one of the five samples tested reached this target lethality for the backstop area (Col. "Spiked Backstop", row corresponding with Recipe Number 1), but all five of the samples tested reached this target lethality for the barrel area (Col. "Spiked Barrel", row corresponding with Recipe Number 1). It should be noted that the spiked backstop test results for Recipe Nos. 1-4 (utilizing the backstop 20 shown in FIG. 2) were tested via direct inoculation whereas the spiked backstop test results for Recipe Nos. 5-14 (utilizing the backstop 120 or 220, shown in FIGS. 3-4) were tested via biological indicators. It also should be noted that "-" symbols indicate that no data is reported for those parameters/samples. The testing method variance aside, the samples tested utilizing backstops 120, 220 achieved target lethality at a much higher rate than the samples utilizing backstop 20. As discussed above, the ridges 150, 250 minimize and/or prevent occluded spaces and instead permit the sterilization agent to completely or substantially reach various components of the pre-filled syringe, particularly the backstop and flange areas.

Different sterilization parameters were also tested with respect to an ingress study. As discussed above, although it is desirable to achieve a target lethality during external sterilization, it is also desirable to reduce, minimize, and/or substantially prevent ingress of the sterilization gas into the drug product chamber. However, the two goals (achieving lethality and minimizing ingress) may serve as competing or counteracting interests. For example, some sterilization parameters that may improve the likelihood of achieving a higher lethality rate may increase the likelihood of having a higher ingress of sterilization gas. Table 5 below and FIG. 7 show results of an ingress study evaluating the effects of different recipes for NO2 based sterilization on the drug product chamber.

TABLE 5

| | Process Parameters | | | | | | NO2 Content in Product (PPM) | | | |
|---|---|---|---|---|---|---|---|---|---|---|
| Test No. | Vac. (Torr) | NO2 Dose (mg/L) | Rel. Hum. (%) | Dwell Time (mins.) | No. of Pulses | No. of Aerat. | Day 1 | Day 14 | Day 30 | Control |
| 1 | 300 | 10 | 75 | 10 | 4 | 35 | 0.157 | — | 0.182 | — |
| 2 | 300 | 10 | 75 | 10 | 8 | 35 | 0.167 | — | 0.404 | — |
| 3 | 20 | 10 | 75 | 10 | 8 | 24 | 0.343 | 0.350 | 0.417 | 0.350 |
| 4 | 20 | 10 | 75 | 10 | 16 | 24 | 0.387 | 0.358 | 0.450 | 0.384 |
| 5 | 20 | 10 | 75 | 10 | 24 | 24 | 0.342 | 0.431 | 0.403 | 0.336 |
| 6 | 100 | 10 | 75 | 10 | 8 | 24 | 0.346 | 0.345 | 0.360 | 0.344 |
| 7 | 100 | 10 | 75 | 10 | 16 | 24 | 0.351 | 0.404 | 0.391 | 0.348 |
| 8 | 100 | 10 | 75 | 10 | 24 | 24 | 0.375 | 0.370 | 0.394 | 0.355 |
| 9 | 300 | 10 | 75 | 10 | 8 | 35 | 0.369 | 0.398 | 0.344 | 0.362 |
| 10 | 300 | 10 | 75 | 10 | 16 | 35 | 0.366 | 0.430 | 0.408 | 0.362 |
| 11 | 300 | 10 | 75 | 10 | 24 | 35 | 0.378 | 0.804 | 1.132 | 0.368 |

The last four columns to the right (collectively labeled "NO2 Content in Product (PPM)") refers to the content of NO2 that ingress into the drug product container, more specifically the content of NO2 that ingress into the drug container, more specifically the NO2 level measured as part per million nitrate in the liquid. The first three columns in this group, labeled, "Day 1", "Day 14", and "Day 30" refer to the ingress as measured at different times after the sterilization process. The last column in this group, labeled "Control", refers to the base level of nitrates (NO3), which is a product of the NO2 and the samples (water for injection). When compared against the Day 1, etc. "exposed" samples, the control "non-exposed" samples provides a baseline differentiation between the exposed sample and the control. For example, for test no. 5, the ingress for day 1 is 0.342 and the control is 0.336, so the difference between an exposed and non-exposed sample may be 0.006 PPM. As another, potentially related parameter, the test method may have an error rate of +1-0.1 PPM.

Although it may be generally desirable to minimize or to substantially or completely prevent ingress, it may be desirable to avoid exceeding an ingress content of 3 PPM, 1 PPM, or another suitable limit. It may be desirable to utilize the "raw" Day 30 values, such as those listed in the column in Table 5 above, or it may be desirable to utilize the "corrected" Day 30 values that have been adjusted based on the Control values. As shown above in Table 5 and in FIG. 7, almost all of the ingress values are below the threshold of 1 PPM (the only exception is the day 30 measurement for Sample 11). As is also shown in the above Table 5 and FIG. 7, varying the different vacuum forces, number of pulses, and number of aerations has varying effects on the ingress measurements. Utilizing these parameters and trends, one may be able to determine sterilization parameters that accomplish a target lethality while staying below a desired ingress level.

As will be recognized, the devices and methods according to the present disclosure may have one or more advantages relative to conventional technology, any one or more of which may be present in a particular embodiment in accordance with the features of the present disclosure included in that embodiment. Other advantages not specifically listed herein may also be recognized as well.

Preferably, the pre-filled syringe does not include an internal coating. The syringe may also comprise a coating on the outer surface of the syringe which is in contact with the environment such as an oxygen barrier coating.

The syringe barrel may have a length of 45 to 85 mm, 60 to 65 mm, or another suitable length. The length of the syringe barrel is the length between the rear end to the outlet to which the needle is attached (but not including the needle, if present).

The syringe barrel may have an internal diameter of 4 to 6.5 mm. If the syringe has a nominal maximum fill volume of 1 ml, the internal diameter of the syringe barrel may be 5.5 to 6.5 mm. If the syringe has a nominal maximum fill volume of 0.5 ml, the internal diameter of the syringe barrel may be 4 to 5 mm.

The wall of the syringe barrel may have a thickness of at least 1 mm; about 1 to 3 mm; about 1.5 to 3 mm; or about 2.4 to 2.8 mm. Due to the thickness of the wall, the sterilizing gas is restricted or prevented from entering interior of the syringe, thereby minimizing or preventing contact with the liquid formulation contained within the pre-filled syringe.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a pre-filled syringe. The pre-filled syringe may have a maximum fill volume, i.e. a volume which can be maximally taken up by the syringe, of 0.3 ml to 1.5 ml, preferably of 0.5 ml to 1.0 ml. The volume of the liquid composition filled into the syringe may be about 0.05 ml to 1.0 ml; about 0.1 ml to 0.5 ml; about 0.14 ml to 0.3 ml; or about 0.15 ml to 0.2 ml. Syringes are typically filled with a larger volume than the volume actually administered to the patient to take into account any dead space within the syringe and the needle and the loss due to the preparation of the syringe for injection. Therefore, the volume which is actually administered to the patient may be between 0.01 ml and 1 ml; between 0.02 and 0.5 ml; between 0.025 and 0.5 ml; between 0.03 ml and 0.05 ml; or 0.05 ml.

In some embodiments, the reservoir of the pre-filled syringe includes a VEGF antagonist. The term "VEGF antagonist" refers to a molecule which specifically interacts with VEGF and inhibits one or more of its biological activities, e.g. its mitogenic, angiogenic and/or vascular permeability activity. It is intended to include both anti-VEGF antibodies and antigen-binding fragments thereof and non-antibody VEGF antagonists. Non-antibody VEGF antagonists include aflibercept, pegaptanib and antibody mimetics. Preferably, the non-antibody VEGF antagonist is aflibercept. Aflibercept which is presently marketed under the name Eylea® and which is also known as VEGF-trap is a recombinant human soluble VEGF receptor fusion protein in which portions of human VEGF receptors 1 and 2 extracellular domains are fused to the Fc portion of human IgGI (Holash et al. (2002) Proc. Natl. Acad. Sci. USA 99(17): 11393-11398; WO 00/75319 Al).

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF). In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed®

(epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 146B7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); Vectibix® (panitumumab), Xgeva® (denosumab), Prolia® (denosumab), Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153, 507); Tysabri® (natalizumab, anti-α4integrin mAb); Valortim® (MDX-1303, anti-*B. anthracis* protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT- 3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, or BPS 804 (Novartis) and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoVEXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A container for use during an external sterilization process of a plurality of drug delivery devices, the container comprising:
    an outer housing including a plurality of openings to permit and/or facilitate entry of sterilization gas into an inner volume thereof; and
    at least one partition at least partially enclosed by the outer housing, the at least one partition including a plurality of first dividers extending in a first direction and a plurality of second dividers extending in a second direction that is generally perpendicular to the first direction, the plurality of first dividers including a first set of notches extending along a height of the first dividers and the plurality of second dividers including a second set of notches extending along a height of the second dividers, the second set of notches being configured to mate with the first set of notches to form the at least one partition,
    wherein the first and second sets of notches facilitate movement between the plurality of first dividers and the plurality of second dividers such that the at least one partition is positionable in an open configuration and a closed configuration while the second set of notches are mated with the first set of notches,
    wherein in the open configuration, the plurality of first dividers and the plurality of second dividers cooperate to define a plurality of chambers configured to receive at least one of the plurality of drug delivery devices, and
    wherein in the closed configuration, the plurality of chambers are substantially completely collapsed.

2. The container as in claim 1, wherein while the at least one partition is positioned in the open configuration, the at least one partition has a length and a width dimension substantially equal to a length and a width dimension of the outer housing.

3. The container as in claim 1, wherein while the at least one partition is positioned in the closed configuration, the at least one partition has a length and/or a width dimension substantially less than a length and/or a width dimension of the outer housing.

4. The container as in claim 1, wherein while the at least one partition is positioned in the closed configuration, the at least one partition has a length and/or a width dimension that is less than half of a corresponding length and/or a width dimension of the outer housing.

5. The container as in claim 1, wherein while the at least one partition is positioned in the closed configuration, the at least one partition has a length and/or a width dimension that is less than one-quarter of a corresponding length and/or a width dimension of the outer housing.

6. The container as in claim 1, wherein while the at least one partition is positioned in the closed configuration, the at least one partition has a length and/or a width dimension that is less than one-eighth of a corresponding length and/or a width dimension of the outer housing.

7. The container as in claim 1, wherein each of the plurality of drug delivery devices includes a pre-filled syringe within a blister pack.

8. The container as in claim 1, wherein each of the plurality of chambers defines a chamber volume, wherein when the at least one partition is positioned in the open configuration, the chamber volume is a non-zero value, wherein when the at least one partition is positioned in the closed configuration, the chamber volume is zero.

9. The container as in claim 1, wherein each of the plurality of chambers includes an opening on each side wall thereof, the opening being configured to permit and/or facilitate distribution of the sterilization gas within the inner volume of the outer housing.

10. The container as in claim 1, wherein the at least one partition and the outer housing cooperate to define a plurality of peripheral chambers along an inner periphery of a plurality of side walls of the outer housing, wherein the plurality of peripheral chambers are smaller in volume than the plurality of chambers.

11. A container for use during an external sterilization process of a plurality of drug delivery devices, the container comprising:
   an outer housing including a plurality of openings to permit and/or facilitate entry of sterilization gas into an inner volume thereof; and
   at least one partition at least partially enclosed by the outer housing, the at least one partition including a plurality of first dividers extending in a first direction and a plurality of second dividers extending in a second direction that is generally perpendicular to the first direction, the plurality of first dividers including a first set of notches extending along a height of the first dividers and the plurality of second dividers including a second set of notches extending along a height of the second dividers, the second set of notches being configured to mate with the first set of notches to form the at least one partition,
   wherein the first and second sets of notches facilitate movement between the plurality of first dividers and the plurality of second dividers such that the at least one partition is positionable in an open configuration and a closed configuration while the second set of notches are mated with the first set of notches,
   wherein, in the open configuration, the at least one partition defines a plurality of chambers, each of the plurality of chambers configured to receive at least two of the plurality of drug delivery devices in a front to back configuration, and
   wherein, in the closed configuration, the plurality of chambers are substantially completely collapsed.

12. The container as in claim 11, wherein the at least one partition defines a plurality of chambers each configured to receive at least three of the plurality of drug delivery devices in a front to back configuration.

13. The container as in claim 11, wherein the at least one partition defines a plurality of chambers each configured to receive at least four of the plurality of drug delivery devices in a front to back configuration.

14. The container as in claim 11, wherein the at least one partition defines a plurality of chambers each configured to receive at least five of the plurality of drug delivery devices in a front to back configuration.

15. The container as in claim 11, wherein the at least one partition is configured to receive at least 180 drug delivery devices.

16. The container as in claim 11, wherein the container includes at least two partitions.

17. The container as in claim 16, wherein the container is configured to receive at least 360 drug delivery devices.

18. The container as in claim 11, wherein the container includes at least four partitions.

19. The container as in claim 18, wherein the container is configured to receive at least 540 drug delivery devices.

20. The container as in claim 19, wherein the container is configured to receive at least 720 drug delivery devices.

21. The container as in claim 11, wherein the plurality of drug delivery devices each include a pre-filled syringe within a blister pack.

* * * * *